United States Patent [19]

Jurgens

[11] Patent Number: 5,576,418

[45] Date of Patent: Nov. 19, 1996

[54] RESORBABLE BIOCOMPATIBLE COPOLYMERS AND THEIR USE

[76] Inventor: Christian Jurgens, Hochallee 19, 2000 Hamburg 13, Germany

[21] Appl. No.: 500,088

[22] Filed: Jul. 10, 1995

Related U.S. Application Data

[62] Division of Ser. No. 906,319, Jun. 29, 1992, Pat. No. 5,466,444.

[51] Int. Cl.$^6$ .......................... C08G 63/08; C08G 63/82; A61K 31/74
[52] U.S. Cl. .................. 528/361; 424/78.08; 424/78.17; 424/78.37; 525/408; 525/411; 525/413; 525/415; 528/354; 528/357
[58] Field of Search ........................ 525/408, 411, 525/413; 528/354, 357, 361; 424/78.08, 78.17, 78.37

[56] References Cited

U.S. PATENT DOCUMENTS

| | | | |
|---|---|---|---|
| 4,045,418 | 8/1977 | Sinclair | 260/78.3 |
| 4,148,871 | 10/1977 | Pitt et al. | 424/426 |
| 4,882,162 | 11/1989 | Ikada et al. | 424/444 |
| 4,981,696 | 1/1991 | Loomis et al. | 424/486 |

FOREIGN PATENT DOCUMENTS

| | | |
|---|---|---|
| 0250994 | 6/1987 | European Pat. Off. . |
| 0368571 | 11/1989 | European Pat. Off. . |
| 0509203 | 2/1992 | European Pat. Off. . |
| 2207635 | 2/1972 | Germany . |
| 3820299 | 6/1988 | Germany . |
| 3928933 | 8/1989 | Germany . |
| 2166354 | 9/1985 | United Kingdom . |
| 8404311 | 4/1984 | WIPO . |
| 9000066 | 6/1989 | WIPO . |
| 9103955 | 9/1989 | WIPO . |
| 9204393 | 10/1991 | WIPO . |

Primary Examiner—Shelley A. Dodson
Attorney, Agent, or Firm—W. Warren Taltavull

[57] ABSTRACT

The invention relates to the use of copolymers of racemic lactide and ε-caprolactone, δ-valerolactone, gamma-decalactone or β-hydroxybutyric acid, prepared by the reaction of the monomers in the molar ratio of lactide to reaction partner of approximately 95–70 to 5–30, with the addition of metal carboxylates, known per se, as initiators at temperatures of approximately 150° C. over a period of time of approximately 16 to 18 hours, for the topical treatment of human or animal skin.

1 Claim, No Drawings

RESORBABLE BIOCOMPATIBLE COPOLYMERS AND THEIR USE

This is a division of application No. 07/906,319, filed Jun. 29, 1992 now U.S. Pat. No. 5,466,494.

FIELD OF THE INVENTION

The invention relates to resorbable, biocompatible copolymers and their use.

BACKGROUND OF THE INVENTION

It is known that high-polymer hydroxycarboxylic acids such as polylactide and polyglycolide are biocompatible and have high compatibility with the body, so that for a rather long time, they have already been used in surgery, as slow-resorbing sutures or as osteosynthetic implants. These high-polymer polycarboxylic acids break down over weeks or months and are broken down by the human or animal body in the usual way via the citric acid cycle or lipometabolism. For this reason, such polymers can also be unobjectionably used as osteosynthetic implants, for example, and in that case they also have the advantage that a second operation for removing the implants is no longer necessary, or is only necessary for the part of the implant that is not of polymer.

From German Published, Non-Examined Patent Application DE-OS 36 20 685, means based on free-flowing to solid oligomeric esters of lactic acid and/or glycolic acid for covering uninjured and/or injured human or animal skin are also known. These preparations substantially comprise the oligomeric esters as resorbable vehicles or film formers and can additionally contain skin-care agents and regenerating, disinfecting, or epithelium-stimulating substances. Film-forming polymers of lactic acid and glycolic acid in solvents such as ethyl acetate, which in addition contain pharmacological active ingredients and can for instance be used as a sprayed-on bandage, are also known from French Patent Application 21 26 270.

From U.S. Pat. Nos. 4,045,418 or 4,148,871, copolymers of lactide and ε-caprolactone are also known, which are biocompatible and can for instance be used as subdermally implantable containers for medications. The compatibility and biodegradability of such containers has been reported, for instance in the Journal of Biomedical Materials Research, Vol. 13, pp. 497–507, 1979 and in Naltrexone: Research Monograph 28, National Institute on Drug Abuse, 1983, written by the team of Colin G. Pitt et al.

A disadvantage of previously known mono- and copolymers of lactic acid and glycolic acid is the fact that they are compounds that are as a rule applied in solutions and are intrinsically relatively hard and not very flexible, so that such sprayed-on films rapidly become brittle and crack after the solvent has evaporated; a further factor is that they do not adhere very well to the surface of the skin or of a wound. On the other hand, as a rule, the previously used polymers of lactide and ε-caprolactone are stiff thermoplastics, suitable for producing containers, for instance, but not for topical application.

Accordingly, there is still a need for biocompatible polymers that can be used on the skin and that do not have the aforementioned disadvantages.

OBJECT AND SUMMARY OF THE INVENTION

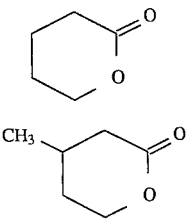

According to the invention, the use of copolymers of racemic lactide and ε-caprolactone, δ-valerolactone, racemic gamma-decalactone or β-hydroxybutyric acid is proposed, where the copolymers are produced by reaction of the monomers, in a molar ratio of lactide to reaction partner of approximately 95–70 to 5–30, with the addition of metal carboxylates known per se as initiators, at temperatures of approximately 150° C. over a period of time of approximately 16 to 48 hours.

The copolymers of the invention can be considered to be polymers and oligomers in terms of their chain lengths, and they are present in the form of a mixture of monomers, oligomers and polymers. They are colorless, transparent compounds, which are viscous to rigid, depending on the molar ratio of the monomer components. The compounds claimed are produced by reaction of the monomers in a molar ratio of lactide to the reaction partner of approximately 95–70 to 5–30, where increasing the lactide proportion leads to an increase in a softening temperature. The reaction takes place with the addition of metal carboxylates, known per se, as initiators at temperatures of approximately 150° C. over a period of time of approximately 16 to 48 hours. The ratio of reaction mixture to initiator is approximately 100:1 to 500:1; increasing this ratio in the reaction increases the proportion of longer molecular chains, and as rule also dictates an increase in the softening point. Tin-II-diethylhexanoate is preferably used as the initiator because it has been found that as a rule, other initiators, known per se, gives a lesser yield or cause clouding or coloration. It was also discovered that a temperature of 150° C. and a reaction time of 16 to 48 hours should not be exceeded, because overly long heating can already cause the onset of degradation of the polymer. The reaction is discontinued after the desired reaction time, either by cooling the reaction mixture or by adding chelating means, for instance. To eliminate remaining monomers, short-chain oligomers, or possibly excess softeners, the reaction composition is as a rule settled out with 600 to 800 times the quantity of alcohol; optionally, the reaction composition can also be washed with water or an aqueous solution, since even a large proportion of monomers, short-chain oligomers or softeners can already be removed by that means.

If desired, softeners can be added to the reaction composition in order to alter the softening temperature and the diffusibility. As softeners, excess caprolactone, tributyl citrate or phthalic acid ester are preferably used. The proportion of softeners should as a rule not exceed 10 to 20%, referred to the weight.

The copolymers of the invention can be put into solution in suitable organic solvents, such as acetic acid, acetone, methylene chloride or THF. Without further additives, they can also be rolled out into films, but films can for instance also be produced by evaporation. Other suitable plastics processing methods may also be employed.

Both the monomers and the polymers are decomposed by hydrolysis in vivo and in vitro. The copolymers and their products of decomposition are medically unobjectionable and are not allergenic. The monomers are further metabolized in vivo via the citric acid cycle or fatty acid metabolism. It has been found that the times for hydrolytic decomposition are shorter, the higher the proportion of lactide.

The polymers claimed according to the invention can be used for manifold medical and cosmetic purposes. One primary area of use is as a surgical incision film. The compounds, present in solution in a suitable solvent such as methylene chloride, acetone or acetic acid, can be readily mixed with known disinfecting agents; a combination with local anesthetics is also possible. If acetic acid is used, a disinfecting action is already achieved because of this solvent.

The most suitable for topical applications are copolymers with a molar ratio between 70:30 to 85:15 and ratio of reaction partner to initiator of approximately 300:1 to 500:1, with a polymerization time of 24 hours. These are washed copolymers; but unwashed copolymers with molar ratios between 80:20 and 90:10 and a ratio of reaction partner to initiator of 100:1 to 400:1 with the same polymerization time are readily usable. The same compounds can be used in the same way for incision films, with the great advantage being, above all, environmental acceptability, simplicity of application, the unlimited nature of the surface areas to be covered, and low-cost manufacture and preparation; a further factor is that in contrast to lactide-glycolide polymers, substantially improved adhesion to the surface of skin and wounds and high flexibility and modelability can be demonstrated. In addition, the preparations according to the invention are striking for their low detachability from aqueous fluids such as blood, lymph and so forth. The natural hydrolytic decomposition of the sprayed-on film takes approximately 3 to 30 weeks in vitro.

The means according to the invention can also be especially favorably used as a liquid glove for handling allergens. Thus they are also a genuine alternative for allergic patients who have allergies to detergents or other washing agents. Because of their long shelf life and good adhesion, such solutions can also be used as adjuvants in camouflage, and particularly when combined with sun protection factors, they can for instance be used as a sun protection that stays on a long time and therefore need not be reapplied all day after swimming.

DETAILED DESCRIPTION

The invention is described in detail below in terms of the examples:

EXAMPLE 1

Preparation of the Copolymers

To prepare the copolymers, D-, L-lactide and ε-caprolactone in a molar ratio of 85:15, corresponding to 70.2 g: 9.8 g, are heated slowly to 150° C. Then, 1.16 ml of tin-II-diethylhexanoate are added as a polymerization initiator (ratio between reaction composition and initiator is 100:1). The polymerization takes place over 24 h at 150° C. in an oil bath. Next, the mixture is cooled down and replenished with ethyl acetate to 1 l at 70° C. This solution is then left in an agitator machine for 36 h and afterward can be used as is.

In a corresponding way, and taking the molar ratios into account, the copolymers of lactide and the other lactones, such as valerolactone, heptalactone, decalactone or those of β-hydroxylic acids such as β-hydroxybutyric acid, can also be prepared.

EXAMPLE 2

Preparation of a Surgical Incision Film

D-, L-lactide and ε-caprolactone in a molar ratio of 90:10 corresponding to 73.5 g: 6.5 g, are heated slowly to 150° C. By the addition of 0.6 ml of tin-II-diethylhexanoate (ratio of reaction composition to initiator =100:1), the polymerization is initiated. The composition is then heated for 24 h at 150° C. in an oil bath. Next, the composition is cooled down and can be replenished with acetic acid to 1 l at 70° C. and processed for 36 h in an agitator machine. The finished solution can then be used directly as a liquid spray.

In the same way, the correspondingly prepared solutions, can be used as a sun protection spray or as a cosmetic foundation. When used for sun protection, conventional UVA and UVB filters, known per se, are admixed with the finished solution.

EXAMPLE 3

Preparation of a Liquid Glove

The solution prepared in accordance with Example 1 is poured into pump sprays or aerosol sprays that are known per se.

I claim:

1. A copolymer prepared by reacting racemic lactide and a monomer selected from the group consisting of ε-caprolactone, δ-valerolactone, γ-decalactone or β-hydroxybutyric acid, wherein the molar ratio of lactide to monomer is approximately 95–70 to 5–30, and wherein the reaction is carried out in the presence of a tin-II-diethylhexanoate initiator in a ratio of lactide and monomer to initiator of from 100 to 1 to 500 to 1, at a temperature of about 150° C. for a period of about 16 to 48 hours.

* * * * *